(12) United States Patent
Stoughton

(10) Patent No.: US 6,274,326 B1
(45) Date of Patent: Aug. 14, 2001

(54) METHOD AND APPARATUS FOR DETECTING PROPER STRIP INSERTION INTO AN OPTICAL REFLECTANCE METER

(75) Inventor: John W. Stoughton, Indianapolis, IN (US)

(73) Assignee: UMM Electronics, Inc., Indianapolis, IN (US)

( * ) Notice: Subject to any disclaimer, the term of this patent is extended or adjusted under 35 U.S.C. 154(b) by 0 days.

(21) Appl. No.: 09/025,053

(22) Filed: Feb. 17, 1998

(51) Int. Cl.[7] .................................................. G01N 33/52
(52) U.S. Cl. .............................. 435/7.1; 422/55; 422/56; 422/58; 435/287.1; 435/287.2; 435/805; 435/970; 436/164; 436/169; 436/514; 436/518; 436/805; 436/810
(58) Field of Search .............................. 422/55, 56, 58; 435/7.1, 287.1, 287.2, 805, 970; 436/514, 518, 164, 169, 805, 810

(56) References Cited

U.S. PATENT DOCUMENTS

| | | | |
|---|---|---|---|
| 4,684,445 | 8/1987 | Seshimoto et al. | 204/1 |
| 4,833,088 * | 5/1989 | DeSimone et al. | 435/289 |
| 4,871,441 | 10/1989 | Tsunekawa et al. | 204/409 |
| 5,189,495 * | 2/1993 | Brunsting et al. | 250/226 |
| 5,231,576 * | 7/1993 | Suzuki et al. | 356/423 |
| 5,277,870 | 1/1994 | Fuller et al. | 422/82.05 |
| 5,526,120 * | 6/1996 | Jina et al. | 356/446 |

* cited by examiner

Primary Examiner—Christopher L. Chin
(74) Attorney, Agent, or Firm—Woodard, Emhardts, Naughton, Moriarty & McNett

(57) ABSTRACT

A method and apparatus for detecting proper strip insertion into an optical reflectance meter. An electrical or electromagnetic device within the optical reflectance meter launches a signal when a test strip is inserted therein. The test strip which is designed for use in such a meter contains a material which enhances the coupling of the signal to a receiver within the meter. The meter then receives the signal and will not produce reading until a signal of a proper level is received. Use of the meter and special test strip of the present invention comprises a more cost effective system for detection of proper test strip insertion which is not dependent upon clean optics as in prior art devices. The present invention therefore ensures reliable protection of strip insertion with the ability to distinguish not only whether the test strip has been inserted incorrectly by the user, but also whether the test strip was designed for use with the meter into which it has been inserted.

10 Claims, 1 Drawing Sheet

METHOD AND APPARATUS FOR DETECTING PROPER STRIP INSERTION INTO AN OPTICAL REFLECTANCE METER

TECHNICAL FIELD OF THE INVENTION

The invention relates generally to blood chemistry monitoring utilizing enzyme-based blood analysis systems, such as blood glucose or cholesterol systems, and more specifically to a method and apparatus for detecting proper strip insertion into an optical reflectance meter.

BACKGROUND OF THE INVENTION

Portable blood glucose monitoring meters were first made available for use in the late 1970's. Portable meters provided patients and health care providers with the means to improve insulin control by permitting them to determine blood glucose levels quickly and with reasonable accuracy, without the need for vein puncture and laboratory analysis. Since the introduction of such meters, improvements to date have produced portable meters offering greater convenience in smaller sizes with more features.

Portable blood glucose monitoring meters today typically utilize disposable test strips, similar to litmus paper, that have applied chemistries that produce a color change when a drop of a patient's capillary blood is applied to the chemistries. In the case of such test strips with chemistries that produce a color change, the strip becomes darker in proportion to the amount of blood glucose present in the blood. In such cases, the strip bearing the patient's blood is inserted into the meter and the color change in the chemistry on the strip is measured using an optical reflectance system within the meter. A microprocessor-based program within the meter then processes the color change measurement and generates a digital read-out of the corresponding concentration, typically in milligrams per decaliter, of blood glucose in the patient's capillary blood. Such meters are commonly known as optical reflectance meters, and they are the most common type of portable blood glucose monitoring meter in use today.

Optical reflectance meters provide accurate results only if the test strip is inserted into the machine properly. Such optical reflectance meters also may not produce valid results if the test strip used was not designed for the meter. Previously, detection of proper test strip insertion in optical reflectance meters has been by means of a second optical channel. This greatly increases the cost of such meters and is therefore undesirable. Additionally, the second optical channel is easily corrupted by the fluid being analyzed (typically blood for consumer devices). Furthermore, an upside down strip is difficult to detect with such methods and often the primary optical channel (which is also easily corrupted by blood) has to be invoked in order to detect this condition. However, even the second optical channel method is unable to distinguish between a characterized test strip and an unknown test strip (wrong analyte, second party strip, etc). This may result in an incorrect reading being given to the user.

There is therefore a need in the blood chemistry monitoring art for a portable blood analysis system which will detect proper test strip insertion and proper test strip design prior to giving a reading to the user. The present invention is directed toward meeting this need.

SUMMARY OF THE INVENTION

The present invention relates to a method and apparatus for detecting proper strip insertion into an optical reflectance meter. An electrical or electromagnetic device within the optical reflectance meter periodically launches a signal in order to detect when a test strip is inserted therein. The test strip which is designed for use in such a meter contains a material which enhances the coupling of the signal to a receiver within the meter. The meter then receives the signal and will not produce a reading until a signal of a proper level is received. Use of the meter and special test strip of the present invention comprises a more cost effective system for detection of proper test strip insertion which is not dependent upon clean optics as in prior art devices. The present invention therefore ensures reliable protection of strip insertion with the ability to distinguish not only whether the test strip has been inserted incorrectly by the user, but also whether the test strip was designed for use with the meter into which it has been inserted.

In one form of the invention, a meter for analyzing a quantity of bodily fluid placed upon a test strip which is inserted into the meter is disclosed, comprising analysis apparatus operative to analyze the bodily fluid and generate a meter output; an electromagnetic core; a first coil wound about the core; a second coil wound about the core; means for impressing a first voltage on the first coil; and means for monitoring a second voltage induced on the second coil, wherein the means for monitoring is operative to activate the analysis apparatus only when the second voltage exceeds a predetermined threshold.

In another form of the invention a meter for analyzing a quantity of bodily fluid placed upon a test strip which is inserted into the meter is disclosed, comprising analysis apparatus operative to analyze the bodily fluid and generate a meter output; a first electrode; a second electrode; means for impressing a first voltage on the first electrode; and means for monitoring a second voltage on the second electrode, wherein the means for monitoring is operative to activate the analysis apparatus only when the second voltage exceeds a predetermined threshold.

In another form of the invention a test strip for use with a meter for analyzing a quantity of bodily fluid placed upon the test strip is disclosed, comprising a test strip foundation; a chemistry area formed on the foundation by applying at least one chemical thereto which will react with the bodily fluid; and a piece of electromagnetic core material attached to the foundation.

In another form of the invention a test strip for use with a meter for analyzing a quantity of bodily fluid placed upon the test strip is disclosed, comprising a test strip foundation; a chemistry area formed on the foundation by applying at least one chemical thereto which will react with the bodily fluid; and a conductive area formed on the foundation.

In another form of the invention a method for determining proper test strip insertion into a meter which analyzes a quantity of bodily fluid placed upon the test strip is disclosed, comprising the steps of: (a) impressing a first signal upon a first conductive member; (b) inducing a second signal upon a second conductive member; (c) monitoring the induced second signal; and (d) activating the meter when the induced second signal exceeds a predetermined threshold.

In another form of the invention a method for determining proper test strip insertion into a meter which analyzes a quantity of bodily fluid placed upon the test strip is disclosed, comprising the steps of: (a) inserting the test strip into meter; (b) determining if the test strip is valid for use with the meter; (c) determining if the test strip has been inserted into the meter with the proper orientation; and (d)

activating the meter only if the test strip is valid and has been inserted with the proper orientation.

DETAILED DESCRIPTION OF THE PREFERRED EMBODIMENTS

Figure 1:
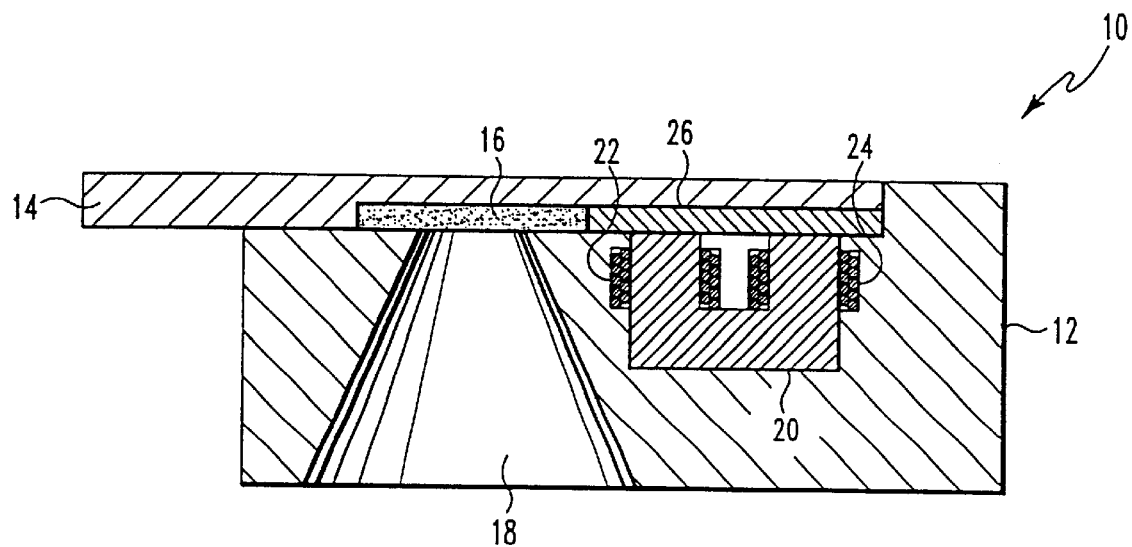
FIG. 1 is a side cross-sectional of a first embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, a cross-sectional view of a first embodiment optical reflectance meter of the present invention is illustrated, and indicated generally at 10. The optical reflectance meter 10 comprises a case 12 which as a slot formed therein into which a test strip 14 may be inserted. The test strip 14 includes a chemistry area 16 to which has been applied a chemistry which will produce a color change when a drop of the patient's capillary blood is applied. Therefore, the user will apply a drop of blood (such as from a finger stick) to the chemistry area 16 prior to inserting the strip 14 into the optical reflectance meter 10. The meter 10 includes an optical read area 18 which is aligned with the chemistry area 16 when the test strip 14 has been properly inserted. It will be appreciated with reference to FIG. 1 that if the test strip 14 is inserted into the optical reflectance meter 10 upside down, there will be a thicker layer (dielectric) of the inert test strip 14 material lying between the chemistry area 16 and the optical read area 18. This layer will change the reading produced by the optics of the reflectance meter 10 to such an extent that the reading is invalid. Also, if the test strip 14 which has been inserted into the optical reflectance meter 10 is not designed for use with the meter 10, then the color change produced by the chemistry area 16 may not be related to the data stored within the optical reflectance meter 10 which converts between sensed color of the chemistry area 16 and indicated blood glucose level. This will result in an invalid measurement.

In order to detect either one of these conditions, the first embodiment optical reflectance meter 10 of the present invention includes a "C" shaped electromagnetic core 20 having first and second coils 22 and 24 wound around respective legs of the core 20. The distal ends of the core 20 legs are placed directly beneath a portion of the test strip 14 which is outside of the blood chemistry area 16. The test strip 14, which is specially designed for use with the optical reflectance meter 10, includes a piece of material of high permeability 26 in the distal end portion of the strip.

An electronic circuit (not shown) within the optical reflectance meter 10 impresses a sinusoidal voltage across the first coil 22. When the test strip 14 is absent from the meter 10, the magnetic core 20 is an open circuit because there is little magnetically permeable material coupling the legs of the "C" shaped core 20. Therefore, the electromagnetic coupling between the first coil 22 and the second coil 24 is minimal. Consequently, the voltage impressed across the second coil 24 is negligible. The same result is obtained if an incorrect test strip (i.e. a test strip without the magnetic material 26 embedded therein) is inserted into the optical reflectance meter 10.

If the correct test strip 14 is used, but is inserted upside down, the magnetic circuit is completed but with rather large air gaps between the magnetic material 26 and the ends of the core 20 legs. Even so, electromagnetic coupling is improved between the first coil 22 and the second coil 24. However, the voltage induced in the second coil 24 will not be at its maximum level. If the test strip 14 is inserted correctly into the optical reflectance meter 10, the electromagnetic circuit will be completed between the legs of the core 20 and magnetic coupling between the first coil 22 and the second coil 24 will be maximized. Consequently, the voltage impressed across the second coil 14 will be at its maximum level. The optical reflectance meter 10 therefore includes electronic circuitry (not shown) which senses the voltage impressed across the second coil 24 in order to determine when the test strip 14 has been inserted correctly. The circuitry will only activate the optical read area 18 upon sensing a voltage on the second coil 24 which is above a predefined minimum threshold level.

Because the signal launched by the first coil 22 will only be transferred to the second coil 24 at an acceptable level if the test strip 14 has been inserted into the optical reflectance meter 10 in the proper way, the first embodiment of the present invention offers distinct advantages over prior art optical reflectance meters. Namely, both incorrect test strip insertion and use of an incorrect test strip may be detected.

Figure 2:
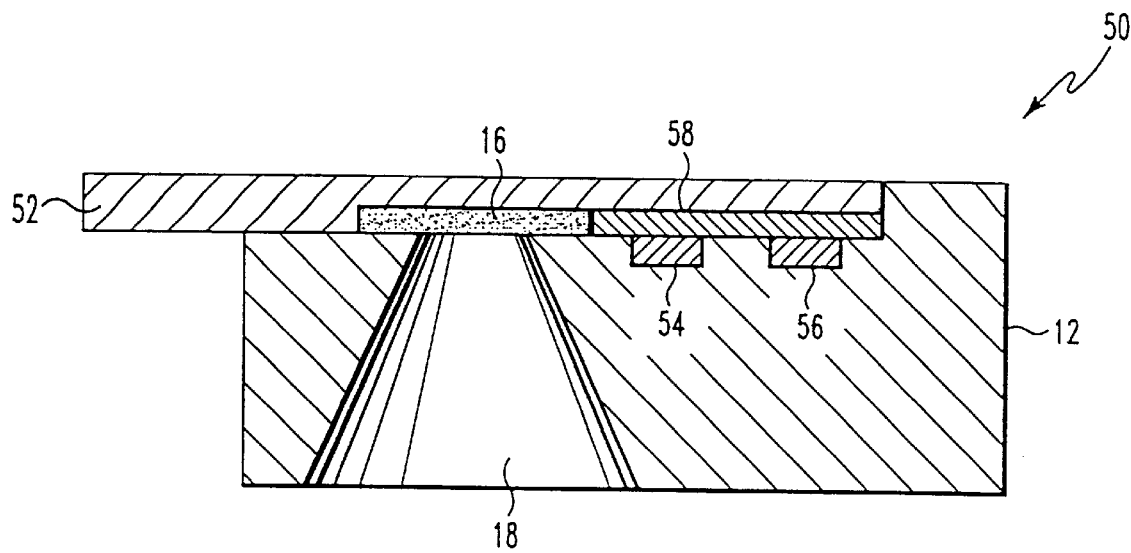
FIG. 2 is a side cross-sectional view of a second embodiment of the present invention.

A second embodiment of the present invention is illustrated in a side cross-sectional view in FIG. 2 and indicated generally at 50. Like the meter 10 of FIG. 1, the optical reflectance meter 50 includes a case 12 which has an opening therein for insertion of the test strip 52. The test strip 52 includes a chemistry area 16 identical to that of the test strip 14. Also, when the test strip 52 is correctly inserted into the optical reflectance meter 50, the chemistry area 16 is aligned with the optical read area 18 in order to detect a color change in the chemistry area 16 related to the blood glucose level.

In order to detect improper test strip insertion, the optical reflectance meter 50 contains two insulated electrodes 54 and 56 which are positioned adjacent the distal end of the test strip 52. The distal end of the test strip 52 includes an area of conductive material 58 which is insulated on its exterior surface. Electronic circuitry (not shown) within the optical reflectance meter 50 applies an AC voltage directly to the first electrode 54, which is capacitively coupled to the second electrode 56. When no test strip 52 is inserted into the optical reflectance meter 50 (or when an improper test strip not containing the conductive material 58 is inserted therein), the coupling between the electrode 54 and the electrode 56 is poor and the voltage impressed on the second electrode 56 is negligible. The distance between the electrodes 54 and 56 determine the amount of coupling and is therefore fixed for any particular design.

When a proper test strip 52 is inserted into the optical reflectance meter 50 but is inserted upside down, a third electrode (the conductive area 58) is effectively introduced into the equivalent electrical circuit, but with an insulating dielectric of inert test strip material between the electrodes. This creates two traditional parallel plate capacitors in series. The first capacitor is formed by the electrode 54 and a portion of the conductive area 58 with the intervening test strip 52 material acting as a dielectric. Similarly, the second capacitor is formed between the second electrode 56 and a portion of the conductive material 58 with the test strip 52 material acting as a dielectric. Because both of these capacitors share the conductive area 58, a series connection of the two capacitors is created. The values of these capacitors is small and (when the first electrode drives a fixed resistance) the resulting signal impressed upon the second electrode 56 can be engineered to be greater in this case than its value when no test strip 52 (or an improper or upside down test strip) is present. This is due to the fact that the capacitance is proportional to the inverse of the distance between the capacitor plates.

When the test strip 52 is inserted correctly, there is a much smaller distance between the conductive area 58 and the electrodes 54 and 56, however the third electrode analysis still holds because the conductive area 58 is covered by a layer of insulation which acts as a dielectric. In this case, the voltage impressed upon the second electrode 56 is always greater than the case where the test strip 52 is inserted upside down or the case where no test strip or an improper test strip is inserted. Therefore, the voltage impressed across the second electrode 56 is an indication of proper test strip insertion status.

It will be appreciated by those skilled in the art that electronic circuitry which is capable of reading the voltage impressed across the second coil 24 or the second electrode 56 and comparing this voltage to a predetermined reference voltage is well known in the art. It is also within the ordinary skill in the art to design a circuit such that the output of such a comparison may be used to trigger the optical reflectance meter to perform a reading of the chemistry area 16. Therefore, the particular design of the electronic circuitry which is used in conjunction with the present invention is not considered to be critical to defining the boundaries of the present invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, application of the present invention is not limited to optical reflectance meters or to meters which measure blood glucose levels, but will find application in any meter type which requires insertion of a test strip.

What is claimed is:

1. A method for enabling a meter, comprising the steps of:
   (a) impressing a first signal upon a first conductive member;
   (b) inducing a second signal upon a second conductive member;
   (c) monitoring the induced second signal; and
   (d) activating the meter when the induced second signal exceeds a predetermined threshold;
   wherein the first conductive member is positioned sufficiently proximate the second conductive member such that a first signal impressed upon the first conductive member can induce a second signal upon the second conductive member.

2. The method of claim 1, wherein the first and second conductive members are electromagnetic coils.

3. The method of claim 1, wherein the induced second signal will exceed the predetermined threshold only when the test strip has been inserted into the meter with a proper orientation.

4. The method of claim 1, further including the step of:
   (e) after (c) and before (d), presenting a strip to the first and second conductive members;
   wherein the first conductive member and the second conductive members are electromagnetically coupled; and
   wherein presenting a strip to the first and second conductive members disturbs the electromagnetic coupling thereof.

5. The method of claim 1 wherein the first conducting member is energetically coupled to the second conducting member.

6. The method of claim 5 wherein the first conducting member is electromagnetically coupled to the second conducting member.

7. The method of claim 1 further including the step of:
   (f) after (c) and before (d), presenting an incompatible strip to the first and second conductive members;
   wherein the first conductive member and the second conductive member are electromagnetically coupled; and
   wherein presenting an incompatible strip to the first and second conductive members disturbs the electromagnetic coupling thereof insufficiently to result in an induced second signal in excess of the predetermined threshold.

8. The method of claim 1 further including the step of:
   (g) after (c) and before (d), presenting a compatible strip to the first and second conductive members;
   wherein the first conductive member and the second conductive member are electromagnetically coupled; and
   wherein presenting a compatible strip to the first and second conductive members disturbs the electromagnetic coupling thereof sufficiently to result in an induced second signal in excess of the predetermined threshold.

9. A method for determining proper test strip insertion into a meter which analyzes a quantity of bodily fluid placed upon the test strip, comprising the steps of:
   (a) inserting the test strip into the meter;
   (b) determining if the test strip is valid for use with the meter;
   (c) determining if the test strip has been inserted into the meter with the proper orientation; and
   (d) activating the meter only if the test strip is valid and has been inserted with the proper orientation.

10. A method for enabling a meter when a compatible test strip is properly inserted, comprising the steps of:
   a) providing an electromagnetically coupled first and second conductive members;
   b) generating the first electromagnetic signal in the first conductive member;
   c) inducing a second electromagnetic signal in the second conductive member;
   d) measuring the strength of the second electromagnetic signal; and
   e) enabling the meter when the induced second electromagnetic signal strength exceeds a predetermined value;
   wherein the induced second electromagnetic signal strength exceeds a predetermined value only when the compatible test strip is inserted between the first and second conductive members.

* * * * *

UNITED STATES PATENT AND TRADEMARK OFFICE
CERTIFICATE OF CORRECTION

PATENT NO.    : 6,274,326 B1
DATED         : August 14, 2001
INVENTOR(S)   : John W. Stoughton It is certified that error appears in the above-identified patent and that said Letters Patent is hereby corrected as shown below:

Column 6,
Line 52, please delete the first occurrence of "the" and insert therefor -- a --.

Signed and Sealed this

Second Day of April, 2002

*Attest:*

JAMES E. ROGAN
*Director of the United States Patent and Trademark Office*

*Attesting Officer*